United States Patent [19]

Mitani

[11] Patent Number: 4,963,656

[45] Date of Patent: Oct. 16, 1990

[54] EMULSIFIED COMPOSITIONS CONTAINING ELASTIN HYDROLYSATE

[75] Inventor: Hiroaki Mitani, Fukuoka, Japan

[73] Assignee: Sansho Seiyaku Co., Ltd., Onojo, Japan

[21] Appl. No.: 194,375

[22] Filed: May 16, 1988

[30] Foreign Application Priority Data

May 30, 1987 [JP] Japan .................. 62-137071

[51] Int. Cl.$^5$ .............. A61K 37/12; A61K 9/107; C07K 15/20
[52] U.S. Cl. ................ 530/353; 435/68.1; 530/407; 514/21
[58] Field of Search ......................... 530/353

[56] References Cited

U.S. PATENT DOCUMENTS

| | | | |
|---|---|---|---|
| 4,179,333 | 12/1979 | Braeumer et al. | 435/69 |
| 4,363,760 | 12/1982 | Cioca | 530/353 |
| 4,419,288 | 12/1983 | Cioca | 530/353 |
| 4,659,740 | 4/1987 | Lisher | 530/353 |

FOREIGN PATENT DOCUMENTS 2804024 8/1979 Fed. Rep. of Germany ......... 514/2
231007 12/1984 Japan .

OTHER PUBLICATIONS

Chem. Abstr. 172434K, vol. 102 (1985), Pola.
Analytical Biochemistry 64, 249–254 (1975) Sandberg et al.
Biochemical and Biophysical Research Communications, 72, No. 4 (1976), Foster et al.

*Primary Examiner*—Howard E. Schain
*Attorney, Agent, or Firm*—Jordan and Hamburg

[57] ABSTRACT

Emulsified compositions comprising an elastin hydrolyzate having a molecular weight not lower than 200,000 (preferably in the range from 1,000,000 to 2,000,000) maintain a stable emulsion state without having to use any other surfactants, and cause sufficient retention of water and moisture on the human skin without having to use any other humectants when employed as cosmetics or external preparations for the skin.

8 Claims, No Drawings

EMULSIFIED COMPOSITIONS CONTAINING ELASTIN HYROLYSATE

BACKGROUND OF THE INVENTION

1. Field of the Invention

This invention relates to highly stable emulsified compositions showing a high degree of water and moisture retention.

2. Description of the Prior Art

Conventional emulsified compositions used as cosmetics (such as emulsified lotions and skin creams) and external preparations for the skin (such as emulsions and ointments) are principally those of the oil-in-water type, prepared by emulsifying, in water, an oily base such as oil and fat, hydrocarbons (e.g., liquid paraffin and ceresin), animal and vegetable oil (e.g., olive oil and beef tallow), and higher fatty acids.

In these compositions, nonionic surfactants of the Span or Tween series are employed to ensure a stable emulsified condition.

The surface-active agents of this type, however, are not preferable as ingredients of cosmetics or external preparations because of their irritative action to the skin and in terms of their feel upon application.

Elastin is a kind of hard protein found in connective tissues of mammalians (particularly in the nuchal ligament and in the middle layer of aortas) together with collagen. Pure elastin isolated from these materials, or soluble elastin obtained by hydrolysis of these materials with an enzyme, has been used in cosmetics and other products as an ingredient to impart the property of water and moisture retention.

Recently, it was found that an elastin hydrolyzate having a molecular weight of 10,000 to 100,000 shows a high effect to stabilize emulsions; and emulsified compositions for cosmetic use containing the same together with a higher alcohol, surface-active agent and others were disclosed (Japanese Patent Kokai No. 59-231007).

The cosmetics using the above-mentioned elastin hydrolyzate having a molecular weight of 10,000 to 100,000 are still insufficient in emulsion stability, requiring further addition of an emulsifier (e.g., surface-active agent) for practical use. In addition, the water and moisture retention is also insufficient, and hence some other humectants need be added. Thus, the problem of disagreeable skin feeling, such as sticky touch, remains unresolved.

SUMMARY OF THE INVENTION

The object of this invention is to provide emulsified compositions free of the above problems, which are excellent in emulsion stability, show a high degree of water and moisture retention, and feel natural and not uncomfortable when applied to the skin.

Thus, this invention relates to an emulsified composition comprising an elastin hydrolyzate having a molecular weight not lower than 200,000.

The elastin hydrolyzate of molecular weight not lower than 200,000 used in this invention is obtained by hydrolysis of elastin present, for example, in the nuchal ligament of mammalians by the action of an enzyme, such as elastase, pepsin and pronase, followed by removal of low-molecular substances. A hydrolyzate having a molecular weight in the range from 1,000,000 to 2,000,000 is particularly suitable for the purpose of this invention.

The emulsified compositions of this invention, primarily used as cosmetics and external preparations for the skin, are emulsions of the oil-in-water type prepared by emulsifying, in water, an oily base such as oil and fat, hydrocarbons (e.g., liquid paraffin, ceresin and microcrystalline wax), animal and vegetable oil (e.g., olive oil, safflower oil and beef tallow), esters (e.g., myristyl myristate and oleyl oleate), higher alcohols (e.g., cetanol and oleyl alcohol) and higher fatty acids (e.g., myristic, palmitic and stearic acids), and further admixing additives commonly employed in cosmetics and external preparations for the skin, such as skin nutrients, preservatives, perfumes and physiologically active substances.

The amount of elastin hydrolyzate having a molecular weight not lower than 200,000 to be used in the emulsified composition of this invention is 0.1 to 10 weight %, preferably 1 to 5 weight %.

The emulsified compositions of this invention may be produced according to the method commonly employed for the manufacture of emulsions. The elastin hydrolyzate having a molecular weight not lower than 200,000 is dissolved in water, and the oily components are added to this aqueous solution to effect emulsification (oil-in-water type emulsions), or the aqueous solution containing the elastin hydrolyzate is added to the oily components to effect emulsification (water-in-oil type emulsions).

The elastin hydrolyzate having a molecular weight not lower than 200,000 is a high-molecular polypeptide composition, which ensures higher emulsion stability than elastin hydrolyzate with a molecular weight less than 100,000, and still shows a sufficiently high degree of water and moisture retention characteristic of elastin.

Hence, the emulsified compositions of this invention comprising such a elastin hydrolyzate maintain a stable emulsion state without having to use any other surfactants, and cause sufficient retention of water and moisture on the human skin without having to use any other humectants. Thus the compositions, when used as cosmetics and external preparations for the skin, rouse no skin irritation or other problems.

Described below is an example of preparing the elastin hydrolyzate having a molecular weight not lower than 200,000 to be used in the emulsified compositions of this invention. (Preparative Example)

Purified elastin (200 g) was mixed well with 1300 g of 1% lactic acid solution, and the mixture was sterilized under pressure at 120° C. for 15 minutes. After cooling the resulting mixture to 15 to 20° C., 9.5 g of pepsin (10,000 units) was added, and enzymic hydrolysis was carried out at 5° C. for 10 to 15 days.

The hydrolyzed solution was filtered, the filtrate was adjusted to pH 7.0 by addition of 20% caustic soda solution, methyl p-oxybenzoate, ethyl p-oxybenzoate and 1,3-butylene glycol were added to concentrations of 0.25%, 0.01% and 5.0%, respectively, and the mixture was heated at 90° C. for ten minutes. After cooling, the resulting mixture was filtered, and the filtrate was allowed to pass through a molecular sieve (M.W.: 200,000) to remove substances having molecular weight less than 200,000.

The final product thus obtained containing elastin hydrolyzate was a slightly turbid solution of pH 6.89. Its coaservation temperature was 32° C, total nitrogen content was 2.01%, and absorbance was 1.074 at 420 nm and 0.352 at 570 nm.

The following Examples will further illustrate the invention.

EXAMPLE 1 (EMULSIFIED LOTION)

Stearic acid: 0.7%
Behenyl alcohol: 0.7%
jojoba oil: 4.0%
Squalane: 4.0%
Vitamin E: 0.1%
Butylparaben: 0.1%
1,3-Butylene glycol: 7.0%
20% Aqueous solution of xanthan gum: 10.0%
Elastin hydrolyzate (obtained in Preparative Example): 10.0%
Pure water: 63.4%
Perfume: proper amount The above components were treated in a homomixer for ten minutes at 7,000 rpm, giving an emulsified lotion.

EXAMPLE 2 (SKIN CREAM)

Stearic acid: 5.0%
Behenyl alcohol: 1.0%
Liquid paraffin: 7.0%
Squalane: 10.0%
jojoba oil: 10.0%
1,3-Butylene glycol: 7.0%
Vitamin E: 0.1%
Butylparaben: 0.1%
Elastin hydrolyzate (obtained in Preparative Example): 10.0%
Pure water: 39.8%
Perfume: proper amount The above components were treated in a homomixer for ten minutes at 7,000 rpm, giving a skin cream.

What is claimed is:

1. An emulsified composition comprising an elastin hydrolyzate having a molecular weight not lower than 200,000.

2. An emulsified composition as in claim 1, wherein said elastin hydrolyzate has an average molecular weight in the range from 1,000,000 to 2,000,000.

3. An emulsified composition as in claim 1, wherein said elastin hydrolyzate is present in an amount ranging from 0.1 to 10% by weight.

4. An emulsified composition as in claim 1, wherein said elastin hydrolyzate is present in an amount ranging from 1 to 5% by weight.

5. An emulsified composition as in claim 1, in a form selected from the group consisting of a cosmetic and an external preparation.

6. An emulsified composition as in claim 1, wherein said elastin hydrolyzate comprises hydrolyzed elastin from a nuchal ligament of a mammalian.

7. An emulsified composition as in claim 1, in a form selected from the group consisting of an emulsified lotion and a skin cream.

8. An emulsified composition as in claim 1, said composition not containing any surfactant or humectant other than said elastin hydrolyzate.

* * * * *